(12) United States Patent
Ahrens et al.

(10) Patent No.: US 8,563,779 B2
(45) Date of Patent: Oct. 22, 2013

(54) (4-TRIFLUOROMETHYL-3-THIOBENZOYL) CYCLOHEXANEDIONES AND USE THEREOF AS HERBICIDES

(75) Inventors: Hartmut Ahrens, Egelsbach (DE); Andreas Van Almsick, Karben (DE); Elmar Gatzweiler, Buedingen (DE); Dieter Feucht, Eschborn (DE); Isolde Haeuser-Hahn, Leverkusen (DE); Stefan Lehr, Liederbach (DE); Christopher Hugh Rosinger, Hofheim (GB)

(73) Assignee: Bayer CropScience AG, Monheim (DE)

( * ) Notice: Subject to any disclaimer, the term of this patent is extended or adjusted under 35 U.S.C. 154(b) by 76 days.

(21) Appl. No.: 13/185,685

(22) Filed: Jul. 19, 2011

(65) Prior Publication Data
US 2012/0021902 A1 Jan. 26, 2012

(30) Foreign Application Priority Data
Jul. 21, 2010 (EP) .................... 10170236

(51) Int. Cl.
| | | |
|---|---|---|
| C07C 315/00 | (2006.01) | |
| C07C 317/00 | (2006.01) | |
| C07C 331/00 | (2006.01) | |
| C07C 49/00 | (2006.01) | |
| C07C 205/00 | (2006.01) | |
| C07D 331/02 | (2006.01) | |
| C07D 409/00 | (2006.01) | |
| C07D 327/04 | (2006.01) | |
| C07D 333/02 | (2006.01) | |
| C07D 323/02 | (2006.01) | |

(52) U.S. Cl.
USPC .......... 568/18; 568/31; 568/75; 568/303; 568/305; 568/306; 568/308; 568/327; 568/331; 549/1; 549/9; 549/13; 549/14; 549/15; 549/29; 549/30; 549/32; 549/49; 549/57; 549/59; 549/62; 549/68; 549/78; 549/83; 549/89; 549/200; 549/346; 549/363; 549/463; 548/100; 548/181; 548/400; 548/466; 548/517; 514/183; 514/210.01; 514/216; 514/224; 514/226.8; 514/299; 514/359; 514/438; 514/449; 514/675; 540/203; 540/214; 540/300; 540/484; 540/553; 540/580; 540/602; 540/604; 540/605; 544/63; 546/112; 546/184; 546/192; 546/242; 546/290

(58) Field of Classification Search
USPC .......... 568/18, 31, 75, 303, 305, 306, 308, 568/327, 331; 514/675, 183, 210.01, 514/211.01, 213.01, 216, 221, 224, 226.8, 514/228.8, 299, 300, 359, 438, 449; 540/203–205, 214, 300, 302, 303, 356, 540/484, 553, 580, 602–605; 544/1, 63; 546/1, 112, 114–116, 184, 192, 242, 546/244, 290; 548/100, 152, 181, 302.7, 548/400, 451, 452, 466, 517; 549/1, 9, 549/13–15, 29, 30, 32, 49, 57, 59, 62, 68, 549/78, 83, 89, 200, 346, 350, 363, 429, 549/463

See application file for complete search history.

(56) References Cited

U.S. PATENT DOCUMENTS

2002/0165096 A1 * 11/2002 Schaetzer et al. ............ 504/314
2011/0053779 A1    3/2011 Ahrens et al.

FOREIGN PATENT DOCUMENTS

| | | | |
|---|---|---|---|
| DE | 199 61 465 | 7/2000 | |
| DE | 19961465 | 7/2000 | |
| DE | 19961465 A1 * | 7/2000 | ............ A01N 43/56 |
| DE | 19961465 A1 * | 7/2000 | ............ A01N 43/56 |
| EP | 0 338 992 | 10/1989 | |
| EP | 0338992 A2 * | 10/1989 | ............ C07C 79/36 |
| WO | 2011/012247 | 2/2011 | |

OTHER PUBLICATIONS

International Search Report Based on PCT/EP2011/062305 Mailed Sep. 22, 2011.

* cited by examiner

*Primary Examiner* — Jane C Oswecki
(74) *Attorney, Agent, or Firm* — Miles & Stockbridge PC

(57) ABSTRACT

A description is given of (4-trifluoromethyl-3-thiobenzoyl) cyclohexanediones of the formula (I) and of their use as herbicides.

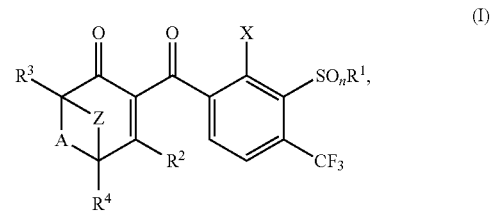

In this formula (I), X, $R^1$, $R^2$, $R^3$, and $R^4$ are radicals such as hydrogen and organic radicals such as alkyl. A and Z are oxygen or alkylene.

13 Claims, No Drawings

(4-TRIFLUOROMETHYL-3-THIOBENZOYL)CYCLOHEXANEDIONES AND USE THEREOF AS HERBICIDES

CROSS REFERENCE TO RELATED APPLICATIONS

This application claims priority from European Application No. 10170236.3, filed Jul. 21, 2010, the content of which is incorporated here in by reference in its entirety.

BACKGROUND

1. Field of the Invention

The invention relates to the technical field of herbicides, more particularly that of herbicides for the selective control of broadleaf and grass weeds in crops of useful plants.

2. Description of Related Art

From various publications it is already known that certain benzoylcyclohexanediones possess herbicidal properties. For instance, EP 0 338 992 A1 and WO 2011/012247 A1 each disclose 2-(3-alkylthiobenzoyl)cyclohexanediones substituted by various radicals. US 2002/165096 A1 and DE 19961465 A1 disclose benzoylcyclohexanediones which carry a directly bonded sulfur radical in position 3 of the phenyl ring.

The herbicidal activity of the compounds known from these publications, however, is frequently inadequate. It is therefore an object of the present invention to provide herbicidally active compounds whose herbicidal properties are improved as compared with those of the compounds known from the prior art.

SUMMARY

It has now been found that certain benzoylcyclohexanediones whose cyclohexanedione ring is bridged and whose phenyl ring carries a thio group in position 3 and a trifluoromethyl group in position 4 are especially suitable as herbicides. The present invention firstly provides (4-trifluoromethyl-3-thio-benzoyl)cyclohexanediones of the formula (I) or salts thereof

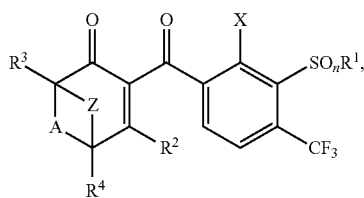

(I)

in which

X is $(C_1$-$C_4)$-alkyl,

A and Z independently of one another are oxygen, —S$(O)_m$—, —N($R^5$)—, carbonyl or $(C_1$-$C_4)$-alkylene which is interrupted by q units from the group consisting of oxygen, —S$(O)_m$—, —N($R^5$)—, and carbonyl, and which is substituted by s radicals $R^6$, $R^1$ is $(C_1$-$C_4)$-alkyl, $R^2$ is hydroxyl, $SR^7$, $NR^8R^6$, $R^3$ and $R^4$ are independently of one another hydrogen or $(C_1$-$C_4)$-alkyl, $R^5$ is hydrogen, $(C_1$-$C_4)$-alkyl, $(C_1$-$C_4)$-alkoxy, $(C_1$-$C_4)$-alkylcarbonyl, $(C_1$-$C_4)$-alkoxycarbonyl, phenylcarbonyl or phenoxycarbonyl, the phenyl ring in the two last-mentioned radicals being substituted by up to p radicals from the group consisting of halogen, nitro, cyano, $(C_1$-$C_4)$-alkyl, $(C_1$-$C_4)$-haloalkyl, $(C_1$-$C_4)$-alkoxy, and $(C_1$-$C_4)$-haloalkoxy, $R^6$ is halogen, $(C_1$-$C_4)$-alkyl, $(C_1$-$C_4)$-haloalkyl, $(C_1$-$C_4)$-alkoxy, $(C_1$-$C_4)$-haloalkoxy or $(C_1$-$C_4)$-alkoxy-$(C_1$-$C_4)$-alkyl, $R^7$ is $(C_1$-$C_4)$-alkyl or is phenyl which is substituted by p radicals from the group consisting of halogen, nitro, cyano, $(C_1$-$C_4)$-alkyl, $(C_1$-$C_4)$-haloalkyl, $(C_1$-$C_4)$-alkoxy, and $(C_1$-$C_4)$-haloalkoxy, $R^8$ is hydrogen, $(C_1$-$C_4)$-alkyl or $(C_1$-$C_4)$-alkoxy, $R^9$ is hydrogen or $(C_1$-$C_4)$-alkyl, or $R^8$ and $R^9$, with the nitrogen atom to which they are attached, form a 5- or 6-membered saturated, partially saturated or fully unsaturated ring which contains m further heteroatoms from the group consisting of oxygen, sulfur, and nitrogen, and which is substituted by up to s halogen atoms and by up to p radicals from the group consisting of cyano, $(C_1$-$C_4)$-alkyl, $(C_1$-$C_4)$-haloalkyl, $(C_1$-$C_4)$-alkoxy, and $(C_1$-$C_4)$-haloalkoxy, m and n independently of one another are 0, 1 or 2, p is 0, 1, 2, 3, 4 or 5, q is 0 or 1, and s is 0, 1, 2, 3, 4, 5, 6, 7 or 8.

DETAILED DESCRIPTION OF A PREFERRED EMBODIMENT

Where $R^2$ is hydroxyl, the compounds of the invention of the formula (I) may exist in the form of different tautomeric structures, depending on external conditions, such as solvent and pH, as follows:

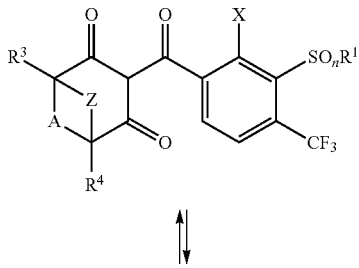

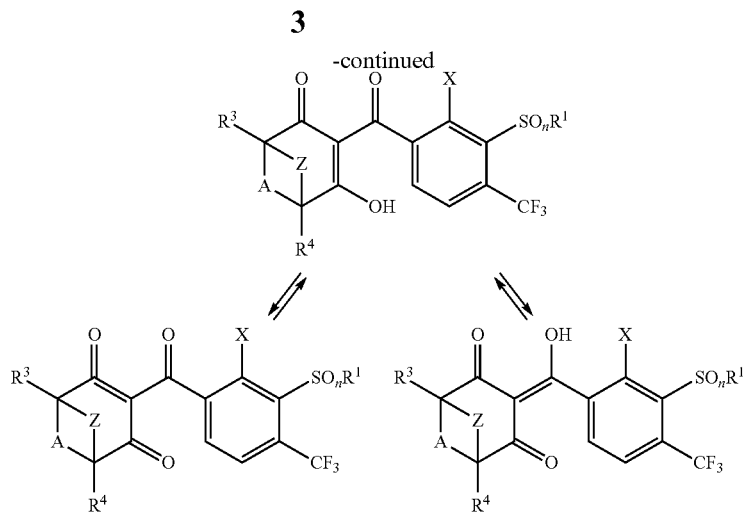

Depending on the nature of the substituents, the compounds of the formula (I) contain an acidic proton which can be removed by reaction with a base. Examples of suitable bases include hydrides, hydroxides, and carbonates of lithium, sodium, potassium, magnesium, and calcium, and also ammonia and organic amines such as triethylamine and pyridine. In addition, salts may be formed by reaction with organic acids, such as formic acid or acetic acid, and with inorganic acids, such as phosphoric, hydrochloric or sulfuric acid. Such salts are likewise provided by the invention.

In the formula (I) and all subsequent formulae, alkyl radicals having more than two carbon atoms may be straight-chain or branched. Alkyl radicals are, for example, methyl, ethyl, n- or iso-propyl, n-, iso-, tert- or 2-butyl, pentyl, hexyl, such as n-hexyl, iso-hexyl and 1,3-dimethylbutyl. Halogen is fluorine, chlorine, bromine or iodine.

Where a group is substituted multiply by radicals, this means that the group in question is substituted by one or more identical or different members from among the radicals specified.

Depending on the nature and attachment of the substituents, the compounds of the formula (I) may be present in the form of stereoisomers. Where, for example, one or more asymmetrically substituted carbon atoms or sulfoxides are present, then enantiomers and diastereomers may occur. Stereoisomers may be obtained from the mixtures resulting from the preparation process by customary separation methods, such as by chromatographic separation methods, for example. It is likewise possible for stereoisomers to be prepared selectively through deployment of stereoselective reactions using optically active starting materials and/or auxiliaries. The invention also relates to all of the stereoisomers and mixtures thereof that are embraced by the formula (I) but not defined specifically.

Preference is given to compounds of the formula (I) in which
X is $(C_1-C_4)$-alkyl,
A and Z are independently of one another oxygen or $(C_1-C_4)$-alkylene,
$R^1$ is $(C_1-C_4)$-alkyl,
$R^2$ is hydroxyl, and
$R^3$ and $R^4$ are independently of one another hydrogen or $(C_1-C_4)$-alkyl.
Particular preference is given to compounds of the formula (I) in which
X is $(C_1-C_4)$-alkyl,
A and Z are each $(C_1-C_4)$-alkylene,
$R^1$ is $(C_1-C_4)$-alkyl,
$R^2$ is hydroxyl, and
$R^3$ and $R^4$ are independently of one another hydrogen or $(C_1-C_4)$-alkyl.

In all formulae given below, the substituents and symbols, unless defined otherwise, have the same meaning as described under formula (I).

Compounds of the invention in which $R^2$ is hydroxyl may be prepared, for example, by the process, indicated in Scheme 1 and known, for example, from WO 03/084912, by base-catalyzed reaction of a benzoyl acid derivative (III), in which $L^1$ is alkoxy or halogen, with a cyclohexanedione (IV) and subsequent rearrangement.

The intermediate (V) may also be prepared by direct reaction of a benzoic acid (II) with a cyclohexanedione (IV) with the addition of an activating condensation agent such as N-(3-dimethylaminopropyl)-N'-ethylcarbodiimide hydrochloride, for example.

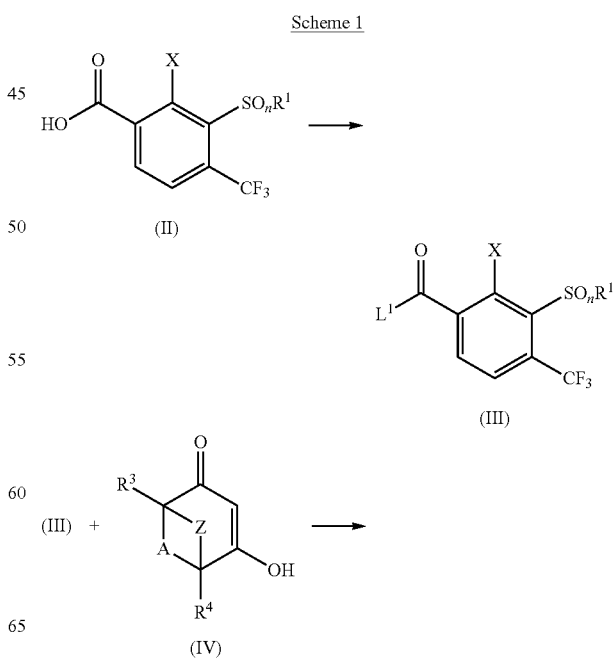

Scheme 1

-continued

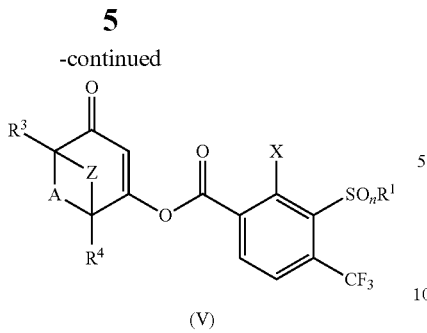

(V)

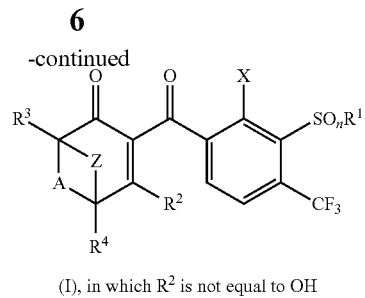

(I), in which $R^2$ is not equal to OH

Cyclohexanediones of the formula (IV) are available commercially or can be prepared in accordance with the process known to the skilled person and described in EP 0 338 992 and WO 2008/0711405, for example. The preparation of the benzoic acids of the formula (II) is known, for example, from WO 2008125214.

The sulfur atom in position 3 of the benzoyl group need not necessarily be oxidized at the stage of the benzoic acid in order to generate compounds with n=1 or 2; for example, an oxidation of this kind at the stage of the enol ester or of the benzoylcyclohexanedione may also be useful.

Collections of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calypso reaction blocks from Barnstead International, Dubuque, Iowa 52004-0797, USA or reaction stations from Radleys, Shirehill, Saffron Walden, Essex, CB11 3AZ, England or MultiPROBE automated workstations from Perkin Elmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the

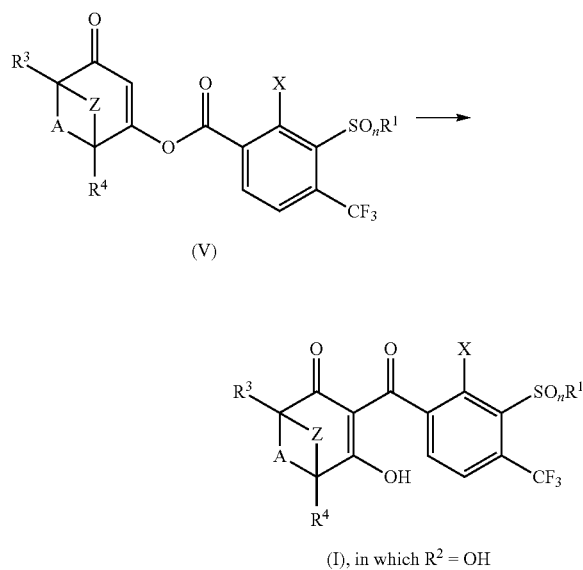

(I), in which $R^2$ = OH

Compounds of the invention in which $R^2$ has a definition other than hydroxyl are usefully prepared in accordance with Scheme 2 from the compounds obtainable in accordance with Scheme 1. Methods of this kind are fundamentally known to the skilled person and described in WO 03/084912, for example.

Scheme 2

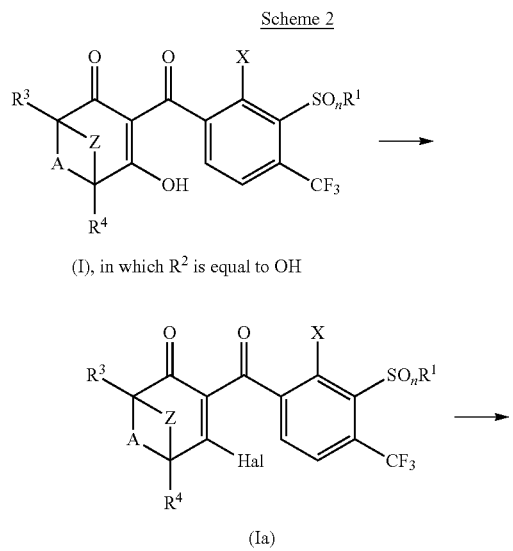

specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editors C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

The compounds of the formula (I) according to the invention (and/or their salts), hereinbelow also referred to together as "compounds according to the invention", have excellent herbicidal efficacy against a broad spectrum of economically important monocotyledonous and dicotyledonous annual weed plants. The active compounds act efficiently even on perennial weeds which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Dicotyledonous broad-leaved weeds of the genera: Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia, or monocotyledonous crops of the genera Allium, Ananas, Asparagus, Avena, Hordeum, Oryza, Panicum, Saccharum, Secale, Sorghum, Triticale, Triticum, Zea, in particular Zea and Triticum, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants which are known or which are yet to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition. Further particular characteristics may lie in tolerance or resistance to abiotic stressors, for example, heat, cold, drought, salt, and ultraviolet radiation.

It is preferred to use the compounds of the formula (I) according to the invention or their salts in economically important transgenic crops of useful plants and ornamentals, for example of cereals such as wheat, barley, rye, oats, millet, rice, cassava and corn or else crops of sugar beet, cotton, soybean, oilseed rape, potato, tomato, peas and other vegetables.

It is possible with preference to employ the compounds of the formula (I) as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP 0221044, EP 0131624). For example, the following have been described in several cases:

the modification, by recombinant technology, of crop plants with the aim of modifying the starch synthesized in the plants (for example WO 92/011376 A, WO 92/014827 A, WO 91/019806 A), transgenic crop plants which are resistant to certain herbicides of the glufosinate type (cf., for example, EP-A-0242236, EP-A-0242246) or of the glyphosate type (WO 92/000377 A) or of the sulfonylurea type (EP-A-0257993, U.S. Pat. No. 5,013,659), or to combinations or mixtures of these herbicides which are resistant as a result of 'gene stacking', such as transgenic crop plants, e.g., corn or soybean, with the trade name or with the designation Optimum™ GAT™ (glyphosate ALS tolerant).

transgenic crop plants, for example cotton, with the capability of producing Bacillus thuringiensis toxins (Bt toxins), which make the plants resistant to certain pests (EP-A-0142924, EP-A-0193259), transgenic crop plants with a modified fatty acid composition (WO 91/013972 A), genetically modified crop plants with novel constituents or secondary metabolites, for example novel phytoalexins, which bring about an increased disease resistance (EPA 0309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example, of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, 2,4 D dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds, or to any combinations of these active compounds.

With particular preference the compounds according to the invention can be used in transgenic crop plants which are resistant to a combination of glyphosates and glufosinates, glyphosates and sulfonylureas or imidazolinones. With very particular preference the compounds according to the invention can be used in transgenic crop plants such as, for example, corn or soybean with the tradename or the designation Optimum™ GAT™ (glyphosate ALS tolerant).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are mandated. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyrdiethyl, cyprosulfamide, isoxadifen-ethyl, cloquintocetmexyl and dichlormid.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are ground finely, for example in customary apparatus such as hammer mills, blower mills and air-jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]-phenyl]-ethanesulfonamide, F-7967, i.e., 3-[7-chloro-5-fluoro-2-(trifluoromethyl)-1H-benzimidazol-4-yl]-1-methyl-6-(trifluoromethyl)pyrimidine-2,4(1H, 3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e., O-(2,4-dimethyl-6-nitrophenyl)-O-ethyl-isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e., 1-(dimethoxyphosphoryl)-ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e., 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methylisothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron-ester, monuron, MT 128, i.e., 6-chloro-N-[(2E)-3-chloroprop-2-en-1-yl]-5-methyl-N-phenylpyridazin-3-amine, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichlorid, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl-(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e., 1-ethoxy-3-methyl-1-oxobut-3-en-2-yl-5-[2-chloro-4-(trifluoromethyl)phenoxy]-2-nitrobenzoate, SYP-300, i.e., 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862 i.e. 3,4-dichloro-N-{2-[(4,6-dimethoxypyrimidin-2-yl)oxy]benzyl}aniline, and also the following compounds:

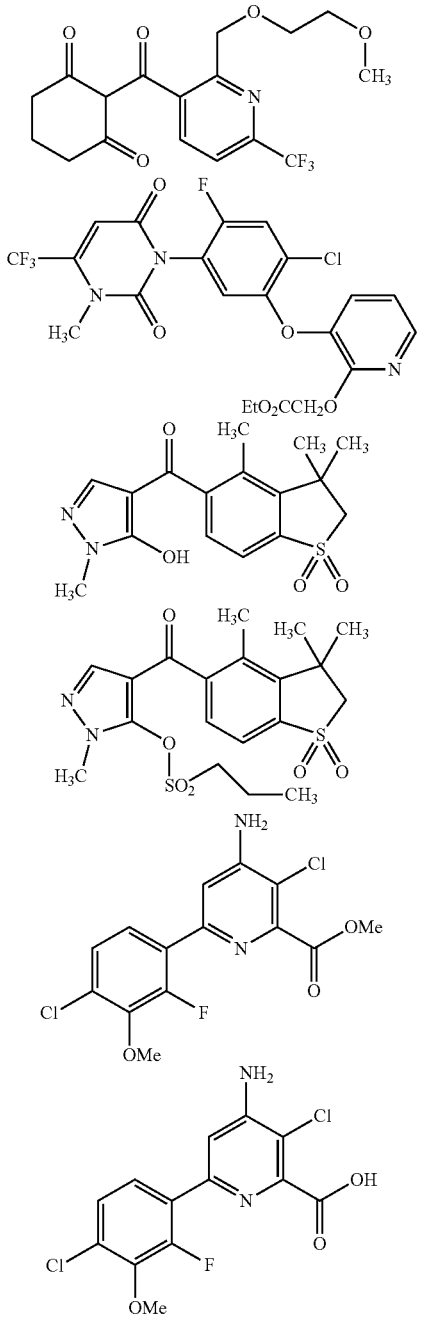

For application, the formulations present in commercial form are, if appropriate, diluted in a customary manner, for example, in the case of wettable powders, emulsifiable concentrates, dispersions and water-dispersible granules, with water. Preparations in the form of dusts, granules for soil application or granules for broadcasting and sprayable solutions are usually not diluted further with other inert substances prior to application.

The required application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably it is between 0.005 and 750 g/ha.

The examples which follow illustrate the invention.

A. CHEMICAL EXAMPLES

Preparation of 3-(2-methyl-3-methylsulfinyl-4-trifluoromethyl)benzoyl)bicyclo[3.2.1]octane-2,4-dione (Tabular Example No. 1-9)

Step 1: Synthesis of 2-methyl-3-(methylsulfinyl)-4-(trifluoromethyl)benzoic acid 1.00 g (4.00 mmol) of 2-methyl-3-(methylthio)-4-(trifluoromethyl)benzoic acid was introduced into 10 ml of glacial acetic acid. The mixture was heated to 50-60° C. At this temperature, 0.35 ml (35% strength, 4.00 mmol) of an aqueous hydrogen peroxide solution was added cautiously dropwise. The mixture was stirred at 60° C. for a number of hours until HPLC analysis no longer indicated any reactant. The reaction mixture was cooled and was worked up by washing with an aqueous 10% strength sodium hydrogensulfite solution. Following analytical verification of the absence of peroxides, the mixture was concentrated. The residue was taken up in water and then 1M hydrochloric acid was added. Extraction was carried out three times with ethyl acetate, and the combined organic phases were thereafter dried and freed from the solvents. 1.00 g of the clean product was isolated.

Step 2: Synthesis of 4-oxobicyclo[3.2.1]oct-2-en-2-yl 2-methyl-3-methylsulfinyl-4-trifluoromethylbenzoat 250 mg (0.94 mmol) of 2-methyl-3-(methylsulfinyl)-4-(trifluoromethyl)benzoic acid were introduced into 25 ml of dry dichloromethane. Thereafter 143 mg (1.03 mmol) of bicyclo[3.2.1]octane-2,4-dione and subsequently, in portions, 216 mg (1.13 mmol) of 1-(3-dimethylaminopropyl)-3-ethylcarbodiimide hydrochloride were added. The mixture was stirred at room temperature for 16 hours and admixed with 5 ml of 1M hydrochloric acid. Following phase separation, the organic phase was freed from the solvent on a rotary evaporator. The residue was purified by chromatography, with 170 mg of clean product being isolated.

Step 3: Synthesis of 3-(2-methyl-3-methylsulfinyl-4-trifluoromethyl)benzoyl)bicyclo[3.2.1]octane-2,4-dione 85.0 mg (0.22 mmol) of 4-oxobicyclo[3.2.1]oct-2-en-2-yl 2-methyl-3-methylsulfinyl-4-trifluoromethylbenzoate were taken up in 15 ml of acetonitrile and admixed with 44.5 mg (0.44 mmol) of triethylamine, a spatula tip-full of potassium cyanide, and eight drops of acetone cyanohydrin. The mixture was stirred at room temperature for 16 h and then concentrated. The residue was admixed with 15 ml of dichloromethane and then with 3 ml of 1M hydrochloric acid. Following phase separation, the organic phase was freed from the solvent. The residue was purified by chromatography. 17 mg of product were isolated.

The examples listed in tables below were prepared in analogy to methods identified above or are obtainable in analogy to methods identified above. These compounds are very particularly preferred.

The abbreviations used have the following meanings:

| Bu = butyl | Et = ethyl | Me = methyl | Pr = propyl |
|---|---|---|---|
| i = iso | s = secondary | t = tertiary | Ph = phenyl |

TABLE 1

Inventive compounds of the formula (I) in which $R^2$ is hydroxyl, A is $(CH_2)$ and Z is $(CH_2)_2$, and $R^3$ and $R^4$ are each hydrogen

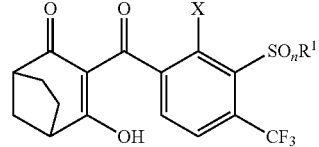

| No. | X | $R^1$ | n | Physical data: $^1$H-NMR: δ [CDCl$_3$] |
|---|---|---|---|---|
| 1-1 | Me | Me | 0 | |
| 1-2 | Me | Et | 0 | 17.39 (s, 1H), 7.61 (d, 1H), 7.11 (d, 1H), 3.16 (m, 1H), 2.89 (m, 1H), 2.76 (q, 2H), 2.48 (s, 3H), 2.27-2.07 (m, 3H), 2.03 (m, 1H), 1.80-1.71 (m, 2H), 1.23 (t, 3H) |
| 1-3 | Me | n-Pr | 0 | |
| 1-4 | Me | i-Pr | 0 | |
| 1-5 | Me | n-Bu | 0 | |
| 1-6 | Me | i-Bu | 0 | |
| 1-7 | Me | s-Bu | 0 | |
| 1-8 | Me | t-Bu | 0 | |
| 1-9 | Me | Me | 1 | 17.23 (s, 1H), 7.62 (d, 1H), 7.22 (d, 1H), 3.18 (m, 1H), 2.98 (s, 3H), 2.88 (m, 1H), 2.72 (s + s, 3H), 2.30-2.09 (m, 3H), 2.09-2.01 (m, 1H), 1.83-1.67 (m, 2H) |
| 1-10 | Me | Et | 1 | 17.24/17.23 (s/s, 1H), 7.63 (d, 1H), 7.21 (d, 1H), 3.42 (m, 1H), 3.17 (m, 1H), 3.02-2.86 (m, 2H), 2.70/2.68 (s/s, 3H), 2.20 (m, 3H), 2.03 (m, 1H), 1.81-1.68 (m, 2H), 1.41 (t, 3H) |
| 1-11 | Me | n-Pr | 1 | |
| 1-12 | Me | i-Pr | 1 | |
| 1-13 | Me | n-Bu | 1 | |
| 1-14 | Me | i-Bu | 1 | |
| 1-15 | Me | s-Bu | 1 | |
| 1-16 | Me | t-Bu | 1 | |
| 1-17 | Me | Me | 2 | 17.11 (s, 1H), 7.82 (d, 1H), 7.33 (d, 1H), 3.23 (s, 3H), 3.18 (m, 1H), 2.87 (m, 1H), 2.61 (s, 3H), 2.31-2.12 (m, 3H), 2.04 (m, 1H), 1.80-1.68 (m, 2H) |
| 1-18 | Me | Et | 2 | 17.10 (s, 1H), 7.83 (d, 1H), 7.32 (d, 1H), 3.32 (q, 2H), 3.18 (m, 1H), 2.88 (m, 1H), 2.60 (s, 3H), 2.30-2.10 (m, 3H), 2.02 (m, 1H), 1.81-1.67 (m, 2H), 1.46 (t, 3H) |
| 1-19 | Me | n-Pr | 2 | |
| 1-20 | Me | i-Pr | 2 | |
| 1-21 | Me | n-Bu | 2 | |
| 1-22 | Me | i-Bu | 2 | |
| 1-23 | Me | s-Bu | 2 | |
| 1-24 | Me | t-Bu | 2 | |
| 1-25 | Et | Me | 0 | 17.38 (s, 1H), 7.6 (d, 1H), 7.1 (d, 1H), 3.15 (m, 1H), 2.92 (s, br, 2H), 2.88 (m, 1H), 2.35 (s, 3H), 2.0-2.3 (m, 4H), 1.75 (m, 2H), 1.15 (t, 3H) |
| 1-26 | Et | Et | 0 | |
| 1-27 | Et | n-Pr | 0 | |
| 1-28 | Et | i-Pr | 0 | |
| 1-29 | Et | n-Bu | 0 | |
| 1-30 | Et | i-Bu | 0 | |
| 1-31 | Et | s-Bu | 0 | |
| 1-32 | Et | t-Bu | 0 | |
| 1-33 | Et | Me | 1 | 17.2 (s, 1H), 7.6 (d, 1H), 7.2 (d, 1H), 3.58 (m, 2H), 3.18 (m, 1H), 3.0 (s, 3H), 2.88 (m, 1H), 1.98-2.3 (m, 4H), 1.65-1.8 (m, 2H), 1.18 (t, 3H) |
| 1-34 | Et | Et | 1 | |
| 1-35 | Et | n-Pr | 1 | |

TABLE 1-continued

Inventive compounds of the formula (I) in which $R^2$ is hydroxyl, A is $(CH_2)$ and Z is $(CH_2)_2$, and $R^3$ and $R^4$ are each hydrogen

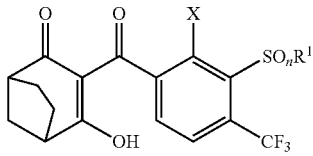

| No. | X | $R^1$ | n | Physical data: $^1$H-NMR: δ [CDCl$_3$] |
|---|---|---|---|---|
| 1-36 | Et | i-Pr | 1 | |
| 1-37 | Et | n-Bu | 1 | |
| 1-38 | Et | i-Bu | 1 | |
| 1-39 | Et | s-Bu | 1 | |
| 1-40 | Et | t-Bu | 1 | |
| 1-41 | Et | Me | 2 | 17.1 (s, 1H), 7.8 (d, 1H), 7.3 (d, 1H), 3.22 (s, 3H), 3.18 (m, 1H), 3.0 (s, vbr, 2H), 2.88 (m, 1H), 2.0-2.3 (m, 4H), 1.75 (m, 2H), 1.22 (t, 3H) |
| 1-42 | Et | Et | 2 | |
| 1-43 | Et | n-Pr | 2 | |
| 1-44 | Et | i-Pr | 2 | |
| 1-45 | Et | n-Bu | 2 | |
| 1-46 | Et | i-Bu | 2 | |
| 1-47 | Et | s-Bu | 2 | |
| 1-48 | Et | t-Bu | 2 | |
| 1-49 | i-Pr | Me | 0 | 17.2 (s, 1H), 7.6 (d, 1H), 7.0 (d, 1H), 4.02 (m, 1H), 3.15 (m, 1H), 2.88 (m, 1H), 2.35 (s, 3H), 2.0-2.3 (m, 4H), 1.75 (m, 2H), 1.22 (d, 6H) |
| 1-50 | i-Pr | Et | 0 | |
| 1-51 | i-Pr | n-Pr | 0 | |
| 1-52 | i-Pr | i-Pr | 0 | |
| 1-53 | i-Pr | n-Bu | 0 | |
| 1-54 | i-Pr | i-Bu | 0 | |
| 1-55 | i-Pr | s-Bu | 0 | |
| 1-56 | i-Pr | t-Bu | 0 | |
| 1-57 | i-Pr | Me | 1 | 16.95 (s, 1H), 7.6 (d, 1H), 7.2 (d, 1H), 4.62 (m, 1H), 3.15 (m, 1H), 3.0 (s, 3H), 2.88 (m, 1H), 2.0-2.3 (m, 4H), 1.75 (m, 2H), 1.28 (d, 6H) |
| 1-58 | i-Pr | Et | 1 | |
| 1-59 | i-Pr | n-Pr | 1 | |
| 1-60 | i-Pr | i-Pr | 1 | |
| 1-61 | i-Pr | n-Bu | 1 | |
| 1-62 | i-Pr | i-Bu | 1 | |
| 1-63 | i-Pr | s-Bu | 1 | |
| 1-64 | i-Pr | t-Bu | 1 | |
| 1-65 | i-Pr | Me | 2 | |
| 1-66 | i-Pr | Et | 2 | |
| 1-67 | i-Pr | n-Pr | 2 | |
| 1-68 | i-Pr | i-Pr | 2 | |
| 1-69 | i-Pr | n-Bu | 2 | |
| 1-70 | i-Pr | i-Bu | 2 | |
| 1-71 | i-Pr | s-Bu | 2 | |
| 1-72 | i-Pr | t-Bu | 2 | |
| 1-73 | n-Pr | Me | 0 | 17.40 (s, 1H), 7.60 (d, 1H), 7.10 (d, 1H), 3.17 (m, 1H), 2.91-2.78 (m, 3H), 2.34 (s, 3H), 2.30-2.10 (m, 3H), 2.02 (m, 1H), 1.78-1.71 (m, 2H), 1.62-1.46 (m, 2H), 0.93 (t, 3H) |
| 1-74 | n-Pr | Et | 0 | |
| 1-75 | n-Pr | n-Pr | 0 | |
| 1-76 | n-Pr | i-Pr | 0 | |
| 1-77 | n-Pr | n-Bu | 0 | |
| 1-78 | n-Pr | i-Bu | 0 | |
| 1-79 | n-Pr | s-Bu | 0 | |
| 1-80 | n-Pr | t-Bu | 0 | |
| 1-81 | n-Pr | Me | 1 | 17.29/17.27 (s/s, 1H), 7.62 (m, 1H), 7.22 (d, 1H), 3.72-3.30 (m, 1H), 3.20 (m, 1H), 3.00 (s, 3H), 2.90 (m, 1H), 2.87-2.42 (m, 1H), 2.31-2.12 (m, 3H), 2.02 (m, 1H), 1.80-1.63 (m, 3H), 1.42 (m, 1H), 0.92 (t, 3H) |
| 1-82 | n-Pr | Et | 1 | |
| 1-83 | n-Pr | n-Pr | 1 | |
| 1-84 | n-Pr | i-Pr | 1 | |

TABLE 1-continued

Inventive compounds of the formula (I) in which $R^2$ is hydroxyl, A is $(CH_2)$ and Z is $(CH_2)_2$, and $R^3$ and $R^4$ are each hydrogen

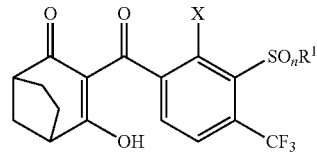

| No. | X | $R^1$ | n | Physical data: $^1$H-NMR: δ [CDCl$_3$] |
|---|---|---|---|---|
| 1-85 | n-Pr | n-Bu | 1 | |
| 1-86 | n-Pr | i-Bu | 1 | |
| 1-87 | n-Pr | s-Bu | 1 | |
| 1-88 | n-Pr | t-Bu | 1 | |
| 1-89 | n-Pr | Me | 2 | 17.14 (s, 1H), 7.81 (d, 1H), 7.31 (d, 1H), 3.24 (s, 3H), 3.20 (m, 1H), 2.88 (m, 1H), 2.31-2.11 (m, 3H), 2.03 (m, 1H), 1.80-1.54 (m, 4H), 0.92 (t, 3H) |
| 1-90 | n-Pr | Et | 2 | |
| 1-91 | n-Pr | n-Pr | 2 | |
| 1-92 | n-Pr | i-Pr | 2 | |
| 1-93 | n-Pr | n-Bu | 2 | |
| 1-94 | n-Pr | i-Bu | 2 | |
| 1-95 | n-Pr | s-Bu | 2 | |
| 1-96 | n-Pr | t-Bu | 2 | |

TABLE 2

Inventive compounds of the formula (I) in which $R^2$ is hydroxyl, A is oxygen, Z is $(CH_2)_2$, $R^3$ is methyl and $R^4$ is hydrogen

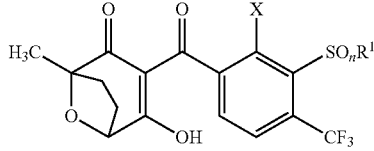

| No. | X | $R^1$ | n | Physical data: $^1$H-NMR: δ [CDCl$_3$] |
|---|---|---|---|---|
| 2-1 | Me | Me | 0 | |
| 2-2 | Me | Et | 0 | |
| 2-3 | Me | n-Pr | 0 | |
| 2-4 | Me | i-Pr | 0 | |
| 2-5 | Me | n-Bu | 0 | |
| 2-6 | Me | i-Bu | 0 | |
| 2-7 | Me | s-Bu | 0 | |
| 2-8 | Me | t-Bu | 0 | |
| 2-9 | Me | Me | 1 | |
| 2-10 | Me | Et | 1 | |
| 2-11 | Me | n-Pr | 1 | |
| 2-12 | Me | i-Pr | 1 | |
| 2-13 | Me | n-Bu | 1 | |
| 2-14 | Me | i-Bu | 1 | |
| 2-15 | Me | s-Bu | 1 | |
| 2-16 | Me | t-Bu | 1 | |
| 2-17 | Me | Me | 2 | |
| 2-18 | Me | Et | 2 | |
| 2-19 | Me | n-Pr | 2 | |
| 2-20 | Me | i-Pr | 2 | |
| 2-21 | Me | n-Bu | 2 | |
| 2-22 | Me | i-Bu | 2 | |
| 2-23 | Me | s-Bu | 2 | |
| 2-24 | Me | t-Bu | 2 | |
| 2-25 | Et | Me | 0 | |
| 2-26 | Et | Et | 0 | |
| 2-27 | Et | n-Pr | 0 | |
| 2-28 | Et | i-Pr | 0 | |
| 2-29 | Et | n-Bu | 0 | |
| 2-30 | Et | i-Bu | 0 | |
| 2-31 | Et | s-Bu | 0 | |
| 2-32 | Et | t-Bu | 0 | |
| 2-33 | Et | Me | 1 | |

TABLE 2-continued

Inventive compounds of the formula (I) in which $R^2$ is hydroxyl, A is oxygen, Z is $(CH_2)_2$, $R^3$ is methyl and $R^4$ is hydrogen

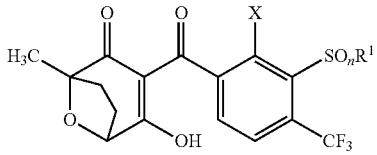

| No. | X | $R^1$ | n | Physical data: $^1$H-NMR: δ [CDCl$_3$] |
|---|---|---|---|---|
| 2-34 | Et | Et | 1 | |
| 2-35 | Et | n-Pr | 1 | |
| 2-36 | Et | i-Pr | 1 | |
| 2-37 | Et | n-Bu | 1 | |
| 2-38 | Et | i-Bu | 1 | |
| 2-39 | Et | s-Bu | 1 | |
| 2-40 | Et | t-Bu | 1 | |
| 2-41 | Et | Me | 2 | |
| 2-42 | Et | Et | 2 | |
| 2-43 | Et | n-Pr | 2 | |
| 2-44 | Et | i-Pr | 2 | |
| 2-45 | Et | n-Bu | 2 | |
| 2-46 | Et | i-Bu | 2 | |
| 2-47 | Et | s-Bu | 2 | |
| 2-48 | Et | t-Bu | 2 | |
| 2-49 | i-Pr | Me | 0 | |
| 2-50 | i-Pr | Et | 0 | |
| 2-51 | i-Pr | n-Pr | 0 | |
| 2-52 | i-Pr | i-Pr | 0 | |
| 2-53 | i-Pr | n-Bu | 0 | |
| 2-54 | i-Pr | i-Bu | 0 | |
| 2-55 | i-Pr | s-Bu | 0 | |
| 2-56 | i-Pr | t-Bu | 0 | |
| 2-57 | i-Pr | Me | 1 | |
| 2-58 | i-Pr | Et | 1 | |
| 2-59 | i-Pr | n-Pr | 1 | |
| 2-60 | i-Pr | i-Pr | 1 | |
| 2-61 | i-Pr | n-Bu | 1 | |
| 2-62 | i-Pr | i-Bu | 1 | |
| 2-63 | i-Pr | s-Bu | 1 | |
| 2-64 | i-Pr | t-Bu | 1 | |
| 2-65 | i-Pr | Me | 2 | |
| 2-66 | i-Pr | Et | 2 | |
| 2-67 | i-Pr | n-Pr | 2 | |
| 2-68 | i-Pr | i-Pr | 2 | |
| 2-69 | i-Pr | n-Bu | 2 | |
| 2-70 | i-Pr | i-Bu | 2 | |
| 2-71 | i-Pr | s-Bu | 2 | |
| 2-72 | i-Pr | t-Bu | 2 | |
| 2-73 | n-Pr | Me | 0 | |
| 2-74 | n-Pr | Et | 0 | |
| 2-75 | n-Pr | n-Pr | 0 | |
| 2-76 | n-Pr | i-Pr | 0 | |
| 2-77 | n-Pr | n-Bu | 0 | |
| 2-78 | n-Pr | i-Bu | 0 | |
| 2-79 | n-Pr | s-Bu | 0 | |
| 2-80 | n-Pr | t-Bu | 0 | |
| 2-81 | n-Pr | Me | 1 | |
| 2-82 | n-Pr | Et | 1 | |
| 2-83 | n-Pr | n-Pr | 1 | |
| 2-84 | n-Pr | i-Pr | 1 | |
| 2-85 | n-Pr | n-Bu | 1 | |
| 2-86 | n-Pr | i-Bu | 1 | |
| 2-87 | n-Pr | s-Bu | 1 | |
| 2-88 | n-Pr | t-Bu | 1 | |
| 2-89 | n-Pr | Me | 2 | |
| 2-90 | n-Pr | Et | 2 | |
| 2-91 | n-Pr | n-Pr | 2 | |
| 2-92 | n-Pr | i-Pr | 2 | |
| 2-93 | n-Pr | n-Bu | 2 | |
| 2-94 | n-Pr | i-Bu | 2 | |
| 2-95 | n-Pr | s-Bu | 2 | |
| 2-96 | n-Pr | t-Bu | 2 | |

TABLE 3

Inventive compounds of the formula (I) in which $R^2$ is phenylthio, A is $(CH_2)$, Z is $(CH_2)_2$, and $R^3$ and $R^4$ are each hydrogen

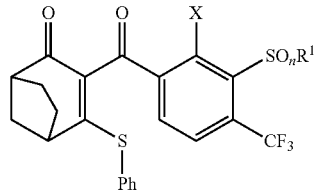

| No. | X | $R^1$ | n | Physical data: $^1$H-NMR: δ [CDCl$_3$] |
|---|---|---|---|---|
| 3-1 | Me | Me | 0 | |
| 3-2 | Me | Et | 0 | |
| 3-3 | Me | n-Pr | 0 | |
| 3-4 | Me | i-Pr | 0 | |
| 3-5 | Me | n-Bu | 0 | |
| 3-6 | Me | i-Bu | 0 | |
| 3-7 | Me | s-Bu | 0 | |
| 3-8 | Me | t-Bu | 0 | |
| 3-9 | Me | Me | 1 | |
| 3-10 | Me | Et | 1 | |
| 3-11 | Me | n-Pr | 1 | |
| 3-12 | Me | i-Pr | 1 | |
| 3-13 | Me | n-Bu | 1 | |
| 3-14 | Me | i-Bu | 1 | |
| 3-15 | Me | s-Bu | 1 | |
| 3-16 | Me | t-Bu | 1 | |
| 3-17 | Me | Me | 2 | |
| 3-18 | Me | Et | 2 | |
| 3-19 | Me | n-Pr | 2 | |
| 3-20 | Me | i-Pr | 2 | |
| 3-21 | Me | n-Bu | 2 | |
| 3-22 | Me | i-Bu | 2 | |
| 3-23 | Me | s-Bu | 2 | |
| 3-24 | Me | t-Bu | 2 | |
| 3-25 | Et | Me | 0 | |
| 3-26 | Et | Et | 0 | |
| 3-27 | Et | n-Pr | 0 | |
| 3-28 | Et | i-Pr | 0 | |
| 3-29 | Et | n-Bu | 0 | |
| 3-30 | Et | i-Bu | 0 | |
| 3-31 | Et | s-Bu | 0 | |
| 3-32 | Et | t-Bu | 0 | |
| 3-33 | Et | Me | 1 | |
| 3-34 | Et | Et | 1 | |
| 3-35 | Et | n-Pr | 1 | |
| 3-36 | Et | i-Pr | 1 | |
| 3-37 | Et | n-Bu | 1 | |
| 3-38 | Et | i-Bu | 1 | |
| 3-39 | Et | s-Bu | 1 | |
| 3-40 | Et | t-Bu | 1 | |
| 3-41 | Et | Me | 2 | |
| 3-42 | Et | Et | 2 | |
| 3-43 | Et | n-Pr | 2 | |
| 3-44 | Et | i-Pr | 2 | |
| 3-45 | Et | n-Bu | 2 | |
| 3-46 | Et | i-Bu | 2 | |
| 3-47 | Et | s-Bu | 2 | |
| 3-48 | Et | t-Bu | 2 | |
| 3-49 | i-Pr | Me | 0 | |
| 3-50 | i-Pr | Et | 0 | |
| 3-51 | i-Pr | n-Pr | 0 | |
| 3-52 | i-Pr | i-Pr | 0 | |
| 3-53 | i-Pr | n-Bu | 0 | |
| 3-54 | i-Pr | i-Bu | 0 | |
| 3-55 | i-Pr | s-Bu | 0 | |
| 3-56 | i-Pr | t-Bu | 0 | |
| 3-57 | i-Pr | Me | 1 | |
| 3-58 | i-Pr | Et | 1 | |
| 3-59 | i-Pr | n-Pr | 1 | |
| 3-60 | i-Pr | i-Pr | 1 | |
| 3-61 | i-Pr | n-Bu | 1 | |
| 3-62 | i-Pr | i-Bu | 1 | |
| 3-63 | i-Pr | s-Bu | 1 | |
| 3-64 | i-Pr | t-Bu | 1 | |
| 3-65 | i-Pr | Me | 2 | |

TABLE 3-continued

Inventive compounds of the formula (I) in which $R^2$ is phenylthio, A is $(CH_2)$, Z is $(CH_2)_2$, and $R^3$ and $R^4$ are each hydrogen

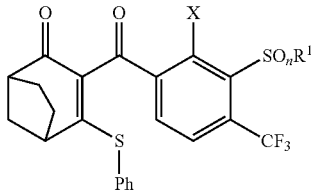

| No. | X | $R^1$ | n | Physical data: $^1$H-NMR: δ [CDCl$_3$] |
|---|---|---|---|---|
| 3-66 | i-Pr | Et | 2 | |
| 3-67 | i-Pr | n-Pr | 2 | |
| 3-68 | i-Pr | i-Pr | 2 | |
| 3-69 | i-Pr | n-Bu | 2 | |
| 3-70 | i-Pr | i-Bu | 2 | |
| 3-71 | i-Pr | s-Bu | 2 | |
| 3-72 | i-Pr | t-Bu | 2 | |
| 3-73 | n-Pr | Me | 0 | |
| 3-74 | n-Pr | Et | 0 | |
| 3-75 | n-Pr | n-Pr | 0 | |
| 3-76 | n-Pr | i-Pr | 0 | |
| 3-77 | n-Pr | n-Bu | 0 | |
| 3-78 | n-Pr | i-Bu | 0 | |
| 3-79 | n-Pr | s-Bu | 0 | |
| 3-80 | n-Pr | t-Bu | 0 | |
| 3-81 | n-Pr | Me | 1 | |
| 3-82 | n-Pr | Et | 1 | |
| 3-83 | n-Pr | n-Pr | 1 | |
| 3-84 | n-Pr | i-Pr | 1 | |
| 3-85 | n-Pr | n-Bu | 1 | |
| 3-86 | n-Pr | i-Bu | 1 | |
| 3-87 | n-Pr | s-Bu | 1 | |
| 3-88 | n-Pr | t-Bu | 1 | |
| 3-89 | n-Pr | Me | 2 | |
| 3-90 | n-Pr | Et | 2 | |
| 3-91 | n-Pr | n-Pr | 2 | |
| 3-92 | n-Pr | i-Pr | 2 | |
| 3-93 | n-Pr | n-Bu | 2 | |
| 3-94 | n-Pr | i-Bu | 2 | |
| 3-95 | n-Pr | s-Bu | 2 | |
| 3-96 | n-Pr | t-Bu | 2 | |

TABLE 4

Inventive compounds of the formula (I) in which $R^2$ is phenylthio, A is oxygen, Z is $(CH_2)_2$, $R^3$ is methyl, and $R^4$ is hydrogen

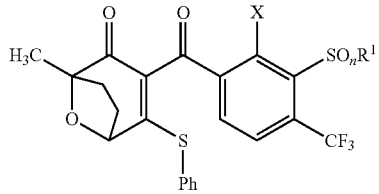

| No. | X | $R^1$ | n | Physical data: $^1$H-NMR: δ [CDCl$_3$] |
|---|---|---|---|---|
| 4-1 | Me | Me | 0 | |
| 4-2 | Me | Et | 0 | |
| 4-3 | Me | n-Pr | 0 | |
| 4-4 | Me | i-Pr | 0 | |
| 4-5 | Me | n-Bu | 0 | |
| 4-6 | Me | i-Bu | 0 | |
| 4-7 | Me | s-Bu | 0 | |
| 4-8 | Me | t-Bu | 0 | |
| 4-9 | Me | Me | 1 | |
| 4-10 | Me | Et | 1 | |
| 4-11 | Me | n-Pr | 1 | |
| 4-12 | Me | i-Pr | 1 | |
| 4-13 | Me | n-Bu | 1 | |
| 4-14 | Me | i-Bu | 1 | |

TABLE 4-continued

Inventive compounds of the formula (I) in which $R^2$ is phenylthio, A is oxygen, Z is $(CH_2)_2$, $R^3$ is methyl, and $R^4$ is hydrogen

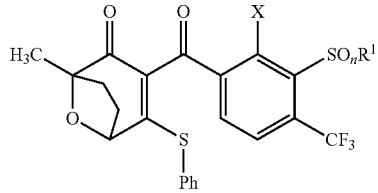

| No. | X | $R^1$ | n | Physical data: $^1$H-NMR: δ [CDCl$_3$] |
|---|---|---|---|---|
| 4-15 | Me | s-Bu | 1 | |
| 4-16 | Me | t-Bu | 1 | |
| 4-17 | Me | Me | 2 | |
| 4-18 | Me | Et | 2 | |
| 4-19 | Me | n-Pr | 2 | |
| 4-20 | Me | i-Pr | 2 | |
| 4-21 | Me | n-Bu | 2 | |
| 4-22 | Me | i-Bu | 2 | |
| 4-23 | Me | s-Bu | 2 | |
| 4-24 | Me | t-Bu | 2 | |
| 4-25 | Et | Me | 0 | |
| 4-26 | Et | Et | 0 | |
| 4-27 | Et | n-Pr | 0 | |
| 4-28 | Et | i-Pr | 0 | |
| 4-29 | Et | n-Bu | 0 | |
| 4-30 | Et | i-Bu | 0 | |
| 4-31 | Et | s-Bu | 0 | |
| 4-32 | Et | t-Bu | 0 | |
| 4-33 | Et | Me | 1 | |
| 4-34 | Et | Et | 1 | |
| 4-35 | Et | n-Pr | 1 | |
| 4-36 | Et | i-Pr | 1 | |
| 4-37 | Et | n-Bu | 1 | |
| 4-38 | Et | i-Bu | 1 | |
| 4-39 | Et | s-Bu | 1 | |
| 4-40 | Et | t-Bu | 1 | |
| 4-41 | Et | Me | 2 | |
| 4-42 | Et | Et | 2 | |
| 4-43 | Et | n-Pr | 2 | |
| 4-44 | Et | i-Pr | 2 | |
| 4-45 | Et | n-Bu | 2 | |
| 4-46 | Et | i-Bu | 2 | |
| 4-47 | Et | s-Bu | 2 | |
| 4-48 | Et | t-Bu | 2 | |
| 4-49 | i-Pr | Me | 0 | |
| 4-50 | i-Pr | Et | 0 | |
| 4-51 | i-Pr | n-Pr | 0 | |
| 4-52 | i-Pr | i-Pr | 0 | |
| 4-53 | i-Pr | n-Bu | 0 | |
| 4-54 | i-Pr | i-Bu | 0 | |
| 4-55 | i-Pr | s-Bu | 0 | |
| 4-56 | i-Pr | t-Bu | 0 | |
| 4-57 | i-Pr | Me | 1 | |
| 4-58 | i-Pr | Et | 1 | |
| 4-59 | i-Pr | n-Pr | 1 | |
| 4-60 | i-Pr | i-Pr | 1 | |
| 4-61 | i-Pr | n-Bu | 1 | |
| 4-62 | i-Pr | i-Bu | 1 | |
| 4-63 | i-Pr | s-Bu | 1 | |
| 4-64 | i-Pr | t-Bu | 1 | |
| 4-65 | i-Pr | Me | 2 | |
| 4-66 | i-Pr | Et | 2 | |
| 4-67 | i-Pr | n-Pr | 2 | |
| 4-68 | i-Pr | i-Pr | 2 | |
| 4-69 | i-Pr | n-Bu | 2 | |
| 4-70 | i-Pr | i-Bu | 2 | |
| 4-71 | i-Pr | s-Bu | 2 | |
| 4-72 | i-Pr | t-Bu | 2 | |
| 4-73 | n-Pr | Me | 0 | |
| 4-74 | n-Pr | Et | 0 | |
| 4-75 | n-Pr | n-Pr | 0 | |
| 4-76 | n-Pr | i-Pr | 0 | |
| 4-77 | n-Pr | n-Bu | 0 | |
| 4-78 | n-Pr | i-Bu | 0 | |
| 4-79 | n-Pr | s-Bu | 0 | |

TABLE 4-continued

Inventive compounds of the formula (I) in which $R^2$ is phenylthio, A is oxygen, Z is $(CH_2)_2$, $R^3$ is methyl, and $R^4$ is hydrogen

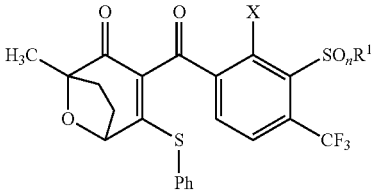

| No. | X | $R^1$ | n | Physical data: $^1$H-NMR: δ [CDCl$_3$] |
|---|---|---|---|---|
| 4-80 | n-Pr | t-Bu | 0 | |
| 4-81 | n-Pr | Me | 1 | |
| 4-82 | n-Pr | Et | 1 | |
| 4-83 | n-Pr | n-Pr | 1 | |
| 4-84 | n-Pr | i-Pr | 1 | |
| 4-85 | n-Pr | n-Bu | 1 | |
| 4-86 | n-Pr | i-Bu | 1 | |
| 4-87 | n-Pr | s-Bu | 1 | |
| 4-88 | n-Pr | t-Bu | 1 | |
| 4-89 | n-Pr | Me | 2 | |
| 4-90 | n-Pr | Et | 2 | |
| 4-91 | n-Pr | n-Pr | 2 | |
| 4-92 | n-Pr | i-Pr | 2 | |
| 4-93 | n-Pr | n-Bu | 2 | |
| 4-94 | n-Pr | i-Bu | 2 | |
| 4-95 | n-Pr | s-Bu | 2 | |
| 4-96 | n-Pr | t-Bu | 2 | |

TABLE 5

Inventive compounds of the formula (I) in which $R^2$ is phenylthio, A is oxygen, Z is $(CH_2)_2$, $R^3$ is hydrogen, and $R^4$ is methyl

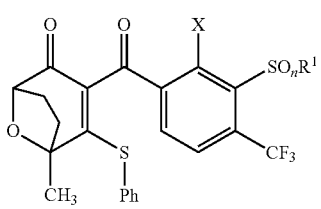

| No. | X | $R^1$ | n | Physical data: $^1$H-NMR: δ [CDCl$_3$] |
|---|---|---|---|---|
| 5-1 | Me | Me | 0 | |
| 5-2 | Me | Et | 0 | |
| 5-3 | Me | n-Pr | 0 | |
| 5-4 | Me | i-Pr | 0 | |
| 5-5 | Me | n-Bu | 0 | |
| 5-6 | Me | i-Bu | 0 | |
| 5-7 | Me | s-Bu | 0 | |
| 5-8 | Me | t-Bu | 0 | |
| 5-9 | Me | Me | 1 | |
| 5-10 | Me | Et | 1 | |
| 5-11 | Me | n-Pr | 1 | |
| 5-12 | Me | i-Pr | 1 | |
| 5-13 | Me | n-Bu | 1 | |
| 5-14 | Me | i-Bu | 1 | |
| 5-15 | Me | s-Bu | 1 | |
| 5-16 | Me | t-Bu | 1 | |
| 5-17 | Me | Me | 2 | |
| 5-18 | Me | Et | 2 | |
| 5-19 | Me | n-Pr | 2 | |
| 5-20 | Me | i-Pr | 2 | |
| 5-21 | Me | n-Bu | 2 | |
| 5-22 | Me | i-Bu | 2 | |
| 5-23 | Me | s-Bu | 2 | |
| 5-24 | Me | t-Bu | 2 | |

TABLE 5-continued

Inventive compounds of the formula (I) in which $R^2$ is phenylthio, A is oxygen, Z is $(CH_2)_2$, $R^3$ is hydrogen, and $R^4$ is methyl

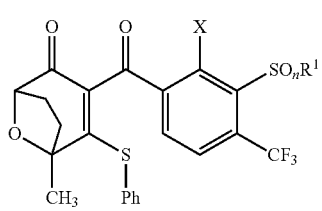

| No. | X | $R^1$ | n | Physical data: $^1$H-NMR: δ [CDCl$_3$] |
|---|---|---|---|---|
| 5-25 | Et | Me | 0 | |
| 5-26 | Et | Et | 0 | |
| 5-27 | Et | n-Pr | 0 | |
| 5-28 | Et | i-Pr | 0 | |
| 5-29 | Et | n-Bu | 0 | |
| 5-30 | Et | i-Bu | 0 | |
| 5-31 | Et | s-Bu | 0 | |
| 5-32 | Et | t-Bu | 0 | |
| 5-33 | Et | Me | 1 | |
| 5-34 | Et | Et | 1 | |
| 5-35 | Et | n-Pr | 1 | |
| 5-36 | Et | i-Pr | 1 | |
| 5-37 | Et | n-Bu | 1 | |
| 5-38 | Et | i-Bu | 1 | |
| 5-39 | Et | s-Bu | 1 | |
| 5-40 | Et | t-Bu | 1 | |
| 5-41 | Et | Me | 2 | |
| 5-42 | Et | Et | 2 | |
| 5-43 | Et | n-Pr | 2 | |
| 5-44 | Et | i-Pr | 2 | |
| 5-45 | Et | n-Bu | 2 | |
| 5-46 | Et | i-Bu | 2 | |
| 5-47 | Et | s-Bu | 2 | |
| 5-48 | Et | t-Bu | 2 | |
| 5-49 | i-Pr | Me | 0 | |
| 5-50 | i-Pr | Et | 0 | |
| 5-51 | i-Pr | n-Pr | 0 | |
| 5-52 | i-Pr | i-Pr | 0 | |
| 5-53 | i-Pr | n-Bu | 0 | |
| 5-54 | i-Pr | i-Bu | 0 | |
| 5-55 | i-Pr | s-Bu | 0 | |
| 5-56 | i-Pr | t-Bu | 0 | |
| 5-57 | i-Pr | Me | 1 | |
| 5-58 | i-Pr | Et | 1 | |
| 5-59 | i-Pr | n-Pr | 1 | |
| 5-60 | i-Pr | i-Pr | 1 | |
| 5-61 | i-Pr | n-Bu | 1 | |
| 5-62 | i-Pr | i-Bu | 1 | |
| 5-63 | i-Pr | s-Bu | 1 | |
| 5-64 | i-Pr | t-Bu | 1 | |
| 5-65 | i-Pr | Me | 2 | |
| 5-66 | i-Pr | Et | 2 | |
| 5-67 | i-Pr | n-Pr | 2 | |
| 5-68 | i-Pr | i-Pr | 2 | |
| 5-69 | i-Pr | n-Bu | 2 | |
| 5-70 | i-Pr | i-Bu | 2 | |
| 5-71 | i-Pr | s-Bu | 2 | |
| 5-72 | i-Pr | t-Bu | 2 | |
| 5-73 | n-Pr | Me | 0 | |
| 5-74 | n-Pr | Et | 0 | |
| 5-75 | n-Pr | n-Pr | 0 | |
| 5-76 | n-Pr | i-Pr | 0 | |
| 5-77 | n-Pr | n-Bu | 0 | |
| 5-78 | n-Pr | i-Bu | 0 | |
| 5-79 | n-Pr | s-Bu | 0 | |
| 5-80 | n-Pr | t-Bu | 0 | |
| 5-81 | n-Pr | Me | 1 | |
| 5-82 | n-Pr | Et | 1 | |
| 5-83 | n-Pr | n-Pr | 1 | |
| 5-84 | n-Pr | i-Pr | 1 | |
| 5-85 | n-Pr | n-Bu | 1 | |
| 5-86 | n-Pr | i-Bu | 1 | |

TABLE 5-continued

Inventive compounds of the formula (I) in which $R^2$ is phenylthio, A is oxygen, Z is $(CH_2)_2$, $R^3$ is hydrogen, and $R^4$ is methyl

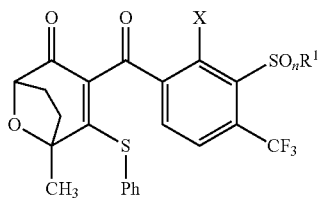

| No. | X | $R^1$ | n | Physical data: $^1$H-NMR: δ [$CDCl_3$] |
|---|---|---|---|---|
| 5-87 | n-Pr | s-Bu | 1 | |
| 5-88 | n-Pr | t-Bu | 1 | |
| 5-89 | n-Pr | Me | 2 | |
| 5-90 | n-Pr | Et | 2 | |
| 5-91 | n-Pr | n-Pr | 2 | |
| 5-92 | n-Pr | i-Pr | 2 | |
| 5-93 | n-Pr | n-Bu | 2 | |
| 5-94 | n-Pr | i-Bu | 2 | |
| 5-95 | n-Pr | s-Bu | 2 | |
| 5-96 | n-Pr | t-Bu | 2 | |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

3. Dispersible Concentrate

A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing 75 parts by weight of a compound of the formula (I), 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill, and granulating the powder in a fluidized bed by spraying on water as granulating liquid.

Water-dispersible granules are also obtained by homogenizing and precomminuting, in a colloid mill, 25 parts by weight of a compound of the formula (I), 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-fluid nozzle.

C. BIOLOGICAL EXAMPLES

1. Pre-emergence Herbicidal Action Against Weed Plants

Seeds or rhizome sections of mono- and dicotyledonous weed plants are set out in pots of 9 to 13 cm in diameter, in sandy loam soil, and are covered with soil. The herbicides, formulated as emulsifiable concentrates or dusts, are applied to the surface of the covering earth in the form of aqueous dispersions or suspensions or emulsions, at a water application rate of 300 to 800 l/ha (converted). The pots are then maintained under glass under optimum conditions for the further cultivation of the plants. After 3 to 4 weeks under optimum growth conditions under glass, the trial plants are scored for the effect of the compounds according to the invention in comparison to compounds disclosed in the prior art. As the results in the comparison tables show, the selected compounds according to the invention exhibit a better herbicidal activity against a broad spectrum of economically important monocotyledonous and dicotyledonous weeds than the compounds disclosed in the prior art.

The meanings of the abbreviations used in the comparison tables below are as follows:

| ABUTH | *Abutilon theophrasti* | ALOMY | *Alopecurus myosuroides* |
|---|---|---|---|
| CYPES | *Cyperus serotinus* | DIGSA | *Digitaria sanguinalis* |
| EPHHL | *Euphorbia heterophylla* | LOLMU | *Lolium multiflorum* |
| MATIN | *Matricaria inodora* | PAPRH | *Papaver rhoeas* |
| PHBPU | *Pharbitis purpureum* | POLCO | *Polygonum convolvulus* |
| VIOTR | *Viola tricolor* | | |

Comparison table 1: Pre-emergence

| Compound | Dose [g a.c./ha] | Herbicidal action against | | |
|---|---|---|---|---|
| | | ALOMY | PHBPU | VIOTR |
| 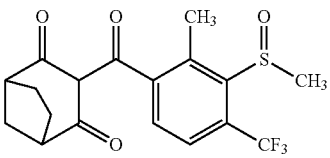 inventive compound No. 1-9 | 320 | 100% | 80% | 100% |
| 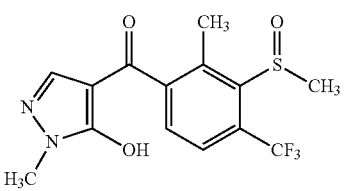 compound No. 1-9, known from WO 2008/125214 | 320 | 70% | 50% | 90% |

Comparison table 2: Pre-emergence

| Compound | Dose [g a.c./ha] | Herbicidal action against | |
|---|---|---|---|
| | | ALOMY | PHBPU |
| 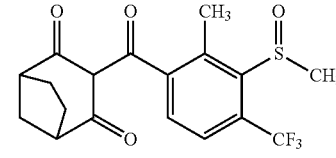 inventive compound No. 1-9 | 320 | 100% | 80% |
| 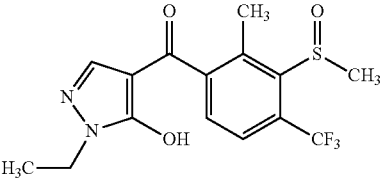 [SMILES: CCn1ncc(C(=O)c2ccc(C(F)(F)F)c(S(C)=O)c2C)c1O] compound No. 2-9, known from WO 2008/125214 | 320 | 70% | 0% |

Comparison table 3: Pre-emergence

| Compound | Dose [g a.c./ha] | Herbicidal action against | | |
|---|---|---|---|---|
| | | ALOMY | LOLMU | VIOTR |
| 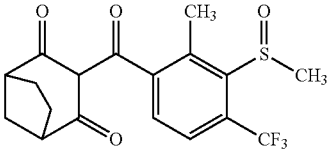 [SMILES: Cc1c(C(=O)C2C(=O)C3CCC(C3)C2=O)ccc(C(F)(F)F)c1S(C)=O] inventive compound No. 1-9 | 320 | 100% | 90% | 100% |

Comparison table 3: Pre-emergence

| Compound | Dose [g a.c./ha] | Herbicidal action against | | |
|---|---|---|---|---|
| | | ALOMY | LOLMU | VIOTR |
| (structure shown) compound No. 3-9, known from WO 2008/125214 | 320 | 60% | 60% | 40% |

Comparison table 4: Pre-emergence

| Compound | Dose [g a.c./ha] | Herbicidal action against | | |
|---|---|---|---|---|
| | | ALOMY | CYPES | POLCO |
| (structure shown) inventive compound No. 1-17 | 320 | 90% | 90% | 100% |
| (structure shown) compound No. 2-17, known from WO 2008/125214 | 320 | 50% | 60% | 60% |

Comparison table 5: Pre-emergence

| Compound | Dose [g a.c./ha] | Herbicidal action against | | |
|---|---|---|---|---|
| | | ALOMY | AMARE | CYPES |
| (structure shown) inventive compound No. 1-17 | 320 | 90% | 100% | 90% |

| Comparison table 5: Pre-emergence | | | | |
|---|---|---|---|---|
| | Dose | Herbicidal action against | | |
| Compound | [g a.c./ha] | ALOMY | AMARE | CYPES |
| compound No. 3-17, known from WO 2008/125214 | 320 | 50% | 90% | 50% |

2. Post-emergence Herbicidal Action Against Weed Plants

Seeds of monocotyledonous and dicotyledonous weed plants are set out in cardboard pots in sandy loam soil, covered with soil, and cultivated under glass under good growth conditions. Two to three weeks after sowing, the trial plants are treated at the three-leaf stage. The compounds according to the invention, formulated as wettable powders or as emulsifiable concentrates, are sprayed onto the surface of the green parts of the plants, at a water application rate of 600 to 800 l/ha (converted). After the trial plants have stood for 3 to 4 weeks under optimum growth conditions under glass, the action of the compounds according to the invention is scored in comparison to compounds disclosed in the prior art. As the results in the comparison tables show, the selected compounds according to the invention exhibit a better herbicidal activity against a broad spectrum of economically important monocotyledonous and dicotyledonous weeds than the compounds disclosed in the prior art.

| Comparison table 6: Post-emergence | | | |
|---|---|---|---|
| | Dose | Herbicidal action against | |
| Compound | [g a.c./ha] | MATIN | PAPRH |
| inventive compound No. 1-9 | 50 | 95% | 95% |
| compound No. 1-9, known from WO 2008/125214 | 50 | 74% | 55% |

| Comparison table 7: Post-emergence | | | |
|---|---|---|---|
| | Dose | Herbicidal action against | |
| Compound | [g a.c./ha] | ALOMY | PHBPU |
| 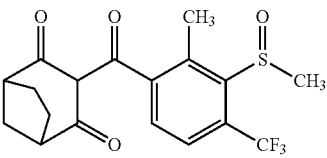 inventive compound No. 1-9 | 80 | 80% | 90% |
| 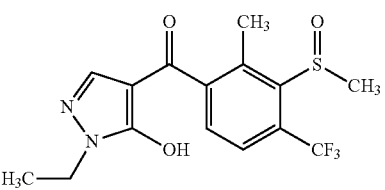 [SMILES: CCn1ncc(C(=O)c2ccc(C(F)(F)F)c(S(C)=O)c2C)c1O] compound No. 2-9, known from WO 2008/125214 | 80 | 60% | 80% |
| Comparison table 8: Post-emergence | | | | |
|---|---|---|---|---|
| | Dose | Herbicidal action against | | |
| Compound | [g a.c./ha] | ABUTH | AMARE | LOLMU |
| 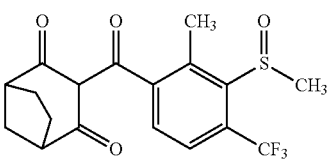 [SMILES: Cc1c(C(=O)C2C(=O)C3CCC(C3)C2=O)ccc(C(F)(F)F)c1S(C)=O] inventive compound No. 1-9 | 80 | 100% | 90% | 80% |
| 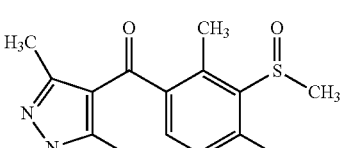 compound No. 3-9, known from WO 2008/125214 | 80 | 80% | 50% | 30% |

Comparison table 9: Post-emergence

| Compound | Dose [g a.c./ha] | Herbicidal action against | |
| --- | --- | --- | --- |
| | | EPHHL | PHBPU |
| inventive compound No. 1-17 | 12.5 | 85% | 85% |
| compound No. 1-17, known from WO 2008/125214 | 12.5 | 45% | 50% |

What is claimed is:

1. A (4-trifluoromethyl-3-thiobenzoyl)cyclohexanedione of formula (I) and/or salt thereof (I)

in which

X is $(C_1-C_4)$-alkyl,

A and Z independently of one another are oxygen, —S$(O)_m$—, —N($R^5$)—, carbonyl or $(C_1-C_4)$-alkylene which is interrupted by q units from the group consisting of oxygen, —S$(O)_m$—, —N($R^5$)—, and carbonyl, and which is substituted by s radicals $R^6$, $R^1$ is $(C_1-C_4)$-alkyl, $R^2$ is hydroxyl, $SR^7$, $NR^8R^9$, $R^3$ and $R^4$ are independently of one another hydrogen or $(C_1-C_4)$-alkyl, $R^5$ is hydrogen, $(C_1-C_4)$-alkyl, $(C_1-C_4)$-alkoxy, $(C_1-C_4)$-alkylcarbonyl, $(C_1-C_4)$-alkoxy-carbonyl, phenylcarbonyl or phenoxycarbonyl, the phenyl ring in the two last-mentioned radicals being substituted by p radicals from the group consisting of halogen, nitro, cyano, $(C_1-C_4)$-alkyl, $(C_1-C_4)$-haloalkyl, $(C_1-C_4)$-alkoxy, and $(C_1-C_4)$-haloalkoxy, $R^6$ is halogen, $(C_1-C_4)$-alkyl, $(C_1-C_4)$-haloalkyl, $(C_1-C_4)$-alkoxy, $(C_1-C_4)$-haloalkoxy or $(C_1-C_4)$-alkoxy-$(C_1-C_4)$-alkyl, $R^7$ is $(C_1-C_4)$-alkyl or is phenyl which is substituted by p radicals from the group consisting of halogen, nitro, cyano, $(C_1-C_4)$-alkyl, $(C_1-C_4)$-haloalkyl, $(C_1-C_4)$-alkoxy, and $(C_1-C_4)$-haloalkoxy, $R^8$ is hydrogen, $(C_1-C_4)$-alkyl or $(C_1-C_4)$-alkoxy, $R^9$ is hydrogen or $(C_1-C_4)$-alkyl, or $R^8$ and $R^9$, with the nitrogen atom to which they are attached, form a 5- or 6-membered saturated, partially saturated or fully unsaturated ring which contains m further heteroatoms from the group consisting of oxygen, sulfur, and nitrogen, and which is substituted by s halogen atoms and by p radicals from the group consisting of cyano, $(C_1-C_4)$-alkyl, $(C_1-C_4)$-haloalkyl, $(C_1-C_4)$-alkoxy, and $(C_1-C_4)$-haloalkoxy, m and n independently of one another are 0, 1 or 2, p is 0, 1, 2, 3, 4 or 5, q is 0 or 1, and s is 0, 1, 2, 3, 4, 5, 6, 7 or 8.

2. A (4-trifluoromethyl-3-thiobenzoyl)cyclohexanedione and/or salt as claimed in claim 1, in which X is $(C_1-C_4)$-alkyl, A and Z are independently of one another oxygen or $(C_1-C_4)$-alkylene, $R^1$ is $(C_1-C_4)$-alkyl, $R^2$ is hydroxyl, and $R^3$ and $R^4$ are independently of one another hydrogen or $(C_1-C_4)$-alkyl.

3. A (4-trifluoromethyl-3-thiobenzoyl)cyclohexanedione and/or salt as claimed in claim 1, in which X is $(C_1-C_4)$-alkyl, A and Z are each $(C_1-C_4)$-alkylene, $R^1$ is $(C_1-C_4)$-alkyl, $R^2$ is hydroxyl, and $R^3$ and $R^4$ are independently of one another hydrogen or $(C_1-C_4)$-alkyl.

4. A method for controlling unwanted plants, which comprises applying an effective amount of at least one compound as claimed in claim 1 to plants and/or to a location of unwanted plant growth.

5. A compound as claimed in claim 1 that is capable of controlling unwanted plants.

6. The compound as claimed in claim 5, that is capable of being used for controlling unwanted plants in crops of useful plants.

7. The compound as claimed in claim 6, wherein the useful plants are transgenic useful plants.

8. A (4-trifluoromethyl-3-thiobenzoyl)cyclohexanedione and/or salt as claimed in claim 1, in which
X is methyl,
A is ($CH_2$),
Z is ($CH_2$)$_2$,
$R^1$ is methyl,
$R^2$ is hydroxyl,
$R^3$ and $R^4$ are independently of one another hydrogen, and
n is 1.

9. A (4-trifluoromethyl-3-thiobenzoyl)cyclohexanedione and/or salt as claimed in claim 1, in which
X is methyl,
A is ($CH_2$),
Z is ($CH_2$)$_2$,
$R^1$ is methyl,
$R^2$ is hydroxyl,
$R^3$ and $R^4$ are independently of one another hydrogen, and
n is 2.

10. A (4-trifluoromethyl-3-thiobenzoyl)cyclohexanedione and/or salt as claimed in claim 1, in which
X is methyl,
A is ($CH_2$),
Z is ($CH_2$)$_2$,
$R^1$ is ethyl,
$R^2$ is hydroxyl,
$R^3$ and $R^4$ are independently of one another hydrogen, and
n is 0.

11. A (4-trifluoromethyl-3-thiobenzoyl)cyclohexanedione and/or salt as claimed in claim 1, in which
X is methyl,
A is ($CH_2$),
Z is ($CH_2$)$_2$,
$R^1$ is methyl,
$R^2$ is hydroxyl,
$R^3$ and $R^4$ are independently of one another hydrogen, and
n is 0.

12. A (4-trifluoromethyl-3-thiobenzoyl)cyclohexanedione and/or salt as claimed in claim 1, in which
X is methyl,
A is ($CH_2$),
Z is ($CH_2$)$_2$,
$R^1$ is ethyl,
$R^2$ is hydroxyl,
$R^3$ and $R^4$ are independently of one another hydrogen, and
n is 2.

13. A (4-trifluoromethyl-3-thiobenzoyl)cyclohexanedione and/or salt as claimed in claim 1, in which
X is ($C_1$-$C_4$)-alkyl,
A and Z are each ($C_1$-$C_4$)-alkylene,
$R^1$ is ($C_1$-$C_4$)-alkyl,
$R^2$ is hydroxyl, and
$R^3$ and $R^4$ are independently of one another hydrogen.

* * * * *